(12) United States Patent
Klootwijk et al.

(10) Patent No.: US 10,126,263 B2
(45) Date of Patent: Nov. 13, 2018

(54) WIDE DYNAMIC RANGE FLUID SENSOR BASED ON NANOWIRE PLATFORM

(71) Applicant: KONINKLIJKE PHILIPS N.V., Eindhoven (NL)

(72) Inventors: Johan Hendrik Klootwijk, Eindhoven (NL); Marcel Mulder, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 538 days.

(21) Appl. No.: 14/435,592

(22) PCT Filed: Oct. 7, 2013

(86) PCT No.: PCT/IB2013/059160
§ 371 (c)(1),
(2) Date: Apr. 14, 2015

(87) PCT Pub. No.: WO2014/060894
PCT Pub. Date: Apr. 24, 2014

(65) Prior Publication Data
US 2016/0003770 A1    Jan. 7, 2016

Related U.S. Application Data

(60) Provisional application No. 61/714,418, filed on Oct. 16, 2012.

(51) Int. Cl.
*G01N 27/00*    (2006.01)
*G01N 27/414*    (2006.01)
(Continued)

(52) U.S. Cl.
CPC ..... *G01N 27/4146* (2013.01); *G01N 33/0031* (2013.01); *H01L 29/0673* (2013.01)

(58) Field of Classification Search
CPC ........... G01N 27/4146; G01N 27/4145; G01N 27/414; G01N 33/0031
See application file for complete search history.

(56) References Cited

U.S. PATENT DOCUMENTS 7,051,945 B2    5/2006 Empedocles
7,963,148 B2    6/2011 Liu
(Continued)

FOREIGN PATENT DOCUMENTS

EP    2378559 A1    10/2011
JP    H04318449    * 11/1992    ............. G01N 27/04
(Continued)

OTHER PUBLICATIONS

C.M. Change, M.H. Hon, I.C. Leu, "Preparation of ZnO Nanorod Arrays With Tailored Defect-Related Characteristics and Their Effect on the Ethanol Gas Sensing Performance", Sensors and Actuators, 2010, p. 15-20.
(Continued)

*Primary Examiner* — Blake A Tankersley

(57) ABSTRACT

A device for detecting a concentration of a substance in a fluid sample includes a substrate; an insulating layer arranged on the substrate; and a plurality of individually electrically addressable semiconducting nanowires arranged on the insulating layer. Each one of the plurality of nanowires is covered by an insulating material and arranged for sensing of the substance through an electrical characteristic of the nanowire. The device further includes a sample compartment for providing the fluid sample in contact with each of the plurality of nanowires. For each of the plurality of nanowires, at least one of the cross sectional dimension, the insulator thickness and the type of insulating material is selected such that each of the nanowires has a different detection range, and such that the dynamic range of the
(Continued)

device is higher than the dynamic range of each of the individual nanowires.

14 Claims, 3 Drawing Sheets

(51) Int. Cl.
*G01N 33/00* (2006.01)
*H01L 29/06* (2006.01)

(56) References Cited

U.S. PATENT DOCUMENTS

| | | | |
|---|---|---|---|
| 8,088,674 B2 | 1/2012 | Ernst | |
| 8,129,725 B2 | 3/2012 | Kunze | |
| 8,169,006 B2 | 5/2012 | Kim | |
| 2007/0269924 A1 | 11/2007 | Gomez | |
| 2008/0093226 A1 | 8/2008 | Briman | |
| 2008/0233675 A1 | 9/2008 | Lee | |
| 2009/0124025 A1* | 5/2009 | Hamilton | B82Y 15/00 436/524 |
| 2009/0152598 A1 | 6/2009 | Baek | |
| 2010/0166614 A1* | 7/2010 | Uchiyama | G01N 27/12 422/98 |
| 2010/0243990 A1 | 9/2010 | Lieber | |
| 2010/0270530 A1 | 10/2010 | Park | |
| 2010/0325073 A1 | 12/2010 | Haick | |
| 2011/0291075 A1* | 12/2011 | Subagyo | B82Y 10/00 257/29 |
| 2012/0134880 A1 | 5/2012 | Kurkina | |
| 2014/0318990 A1* | 10/2014 | Star | B82Y 15/00 205/787.5 |

FOREIGN PATENT DOCUMENTS

| | | |
|---|---|---|
| JP | 2009229341 A | 10/2009 |
| WO | 0248701 A2 | 6/2002 |

OTHER PUBLICATIONS

Alireza Kargar, "Sensitivity Analysis of Silicon Nanowire Chemical Sensor", Department of Electrical Engineering, Shiraz University, Shiraz, Iran, p. 1-4, 2008.

L. Liao, H.V. Lu, J.C. Li, H. He, D.F. Wang, D.J. Fu. C. Liu and W.F. Zhang, "Size Dependence of Gas Sensitivity of ZnO Nanorods", J. Phys. Chem. C 2007, 111, 1900-1903.

Gengfeng Zheng, Fernando Patolsky, Yi Cui, Wayne U. Wang, and Charles M. Lieber, "Multiplexed Electrical Detection of Cancer Markers With Nanowire Sensor Arrays", Nature Biotechnology, vol. 23, No. 10, Oct. 2005, 1294-1301.

Jong-In Hahm and Charles M. Lieber, "Direct Ultrasensitive Electrical Detection of CNA and DNA Sequence Variations Using Nanowire Nanosensors", Nano Letter 2004, vol. 4, No. 1, pp. 51-54.

Pradeep R. Nair and Muhammad A. Alam, "Screening-Limited Response of Nanobiosensors", Nano Letter, 2008, vol. 8, No. 5, pp. 1281-1285.

Daihua Zhang, Zuqin Liu, Chao Li, Tao Tang, Xiaolei Liu, Song Han, Bo Lei and Chongwu Zhou, "Detection of NO2 Down to PPB Levels Using Individual and Multiple In2O3 Nanowire Devices", Nano Letter, 2004, vol. 4, No. 10, pp. 1919-1924.

Zhifu Liu, Toshinai Yamazaki, Yanbai Shen, Toshio Kikuta, Noriyuki Nakatani and Tokimasa Kawabata, "Room Temperature Gas Sensing of P-Type TeO2 Nanowires" Applied Physics Letters 90, 2007, pp. 173119-1 Thru 173119-3.

Yi Cui, Qingqiao Wei, Hongkun Park and Charles M. Lieber, "Nanowire Nanosensors for Highly Sensitive and Selective Detection of Biological and Chemical Species", Science, vol. 293, Aug. 17, 2001, pp. 1289-1292.

M. Tonezzer and N.V. Hieu, "Size-Dependent Response of Single-Nanowire Gas Sensors", Sensors and Actuators B 163, 2012, pp. 146-152.

Dan Yaping, Setephane Evoy and A.TT. Charlie Johnson, "Chemical Gas Sensors Based on Nanowires", Department of Electrical & Systems Eng., Universtiy of Pennsylvania, 2008, pp. 1-34.

* cited by examiner

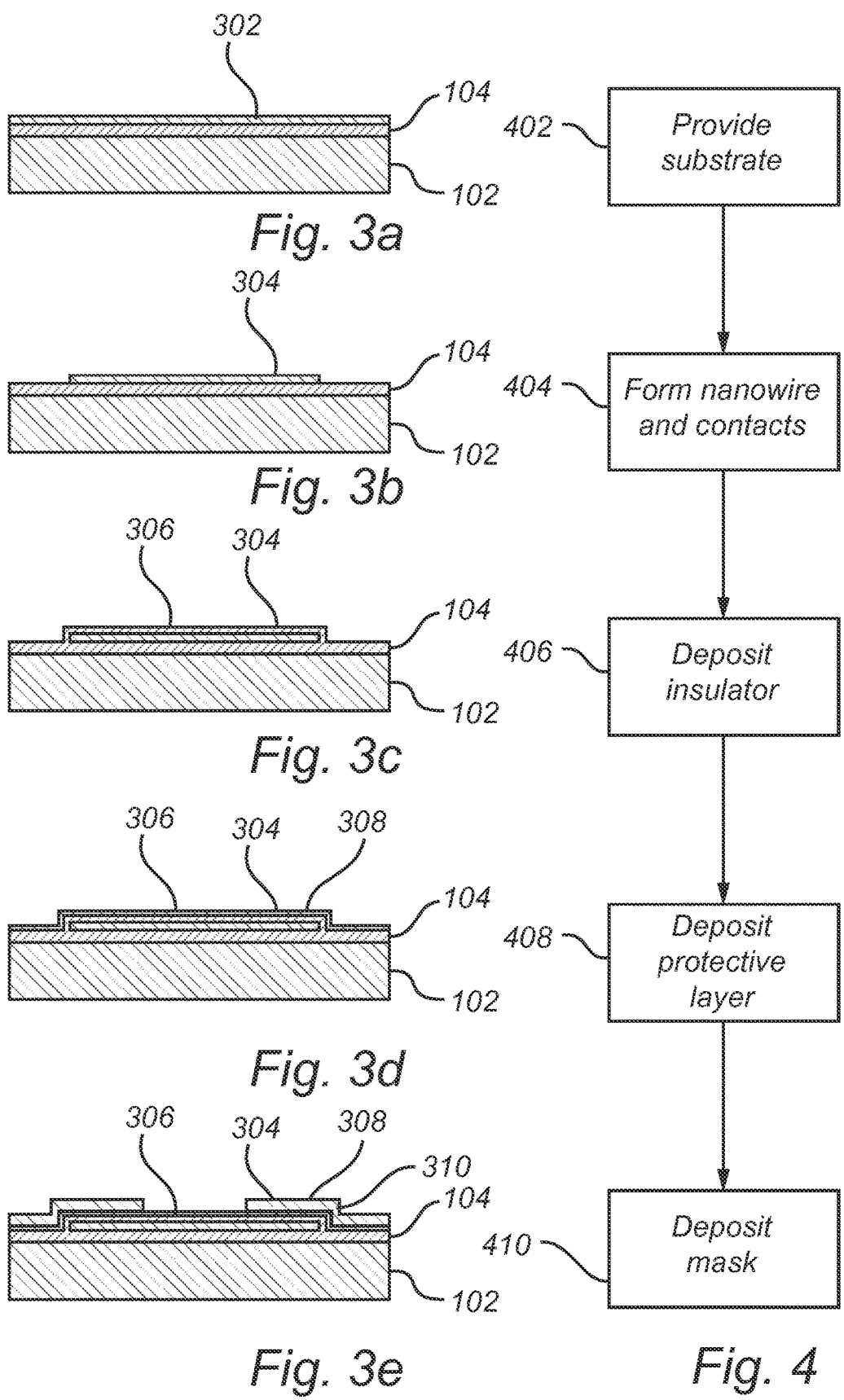

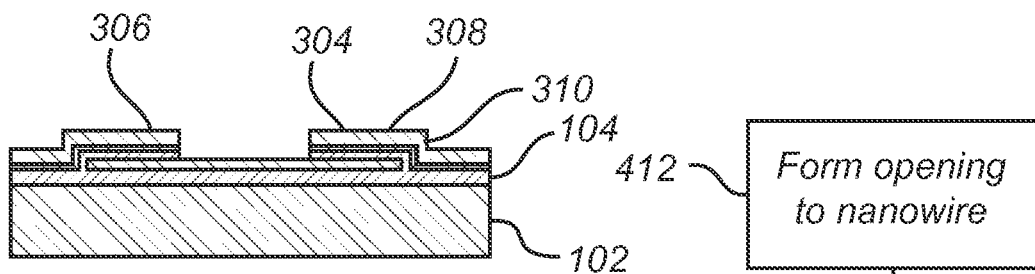
Fig. 3f
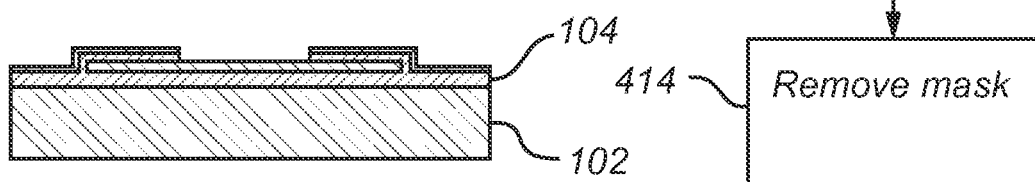
Fig. 3g
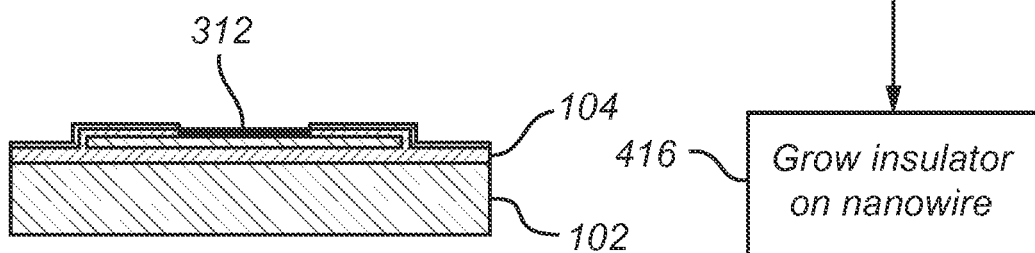
Fig. 3h
Fig. 4

WIDE DYNAMIC RANGE FLUID SENSOR BASED ON NANOWIRE PLATFORM

This application is the U.S. National Phase application under 35 U.S.C. § 371 of International Application No. PCT/IB2013/059160, filed on Oct. 7, 2013, which claims the benefit of U.S. Provisional Application No. 61/714,418 filed on Oct. 16, 2012. These applications are hereby incorporated by reference herein.

FIELD OF THE INVENTION

The present invention relates to a device for detecting a concentration of a substance in a fluid. In particular, the present invention relates to a nanowire-based device.

BACKGROUND OF THE INVENTION

Sensors for detection of biological substances based on nanoscale field-effect transistors, such as for example silicon nanowire FETs and carbon nanotubes with properly functionalized surfaces, have enormous potential for very sensitive detection of minute (down to femtomolar) concentrations of biomolecules such as proteins and DNA. In addition, when proper interface layers are applied through functionalization of the surface in contact with the active substance, these devices are potentially interesting for sensing gasses as well.

In all applications where the nanoscale field-effect transistor is used there is a strong desire for sensing multiple target molecules simultaneously. In a liquid or gas environment, the use of a reference transistor is of crucial and critical importance in order to compensate for time related drift.

For many applications of gas sensors, such as indoor air quality (IAQ) management, HVAC, asthma, cardiovascular diagnosis, and greenhouse control, a high sensitivity combined with a wide dynamic range is required. Mass spectrometry is the standard method for gas detection. This technique is sensitive, selective and has a wide dynamic range, but is also costly and sizable. Alternatively, optical detection, more specifically absorption spectroscopy in the infra red (IR), is being used as a gas sensor. This technique is sensitive and selective, but one module can only detect one type of molecule and the measurement equipment is costly and sizable. Electrochemical detection can also be used but does not provide the proper sensitivity or the selectivity.

US2010/0243990 discloses a nanowire-based sensor device for detecting bio-molecules. The devices are based on a silicon nanowire field-effect transistor, where the nanowire can be either n-type or p-type impurity doped. The surface of the nanowire is functionalized by molecules that specifically couple to their targeted counterparts. The charges on the target molecules affect the conductivity of the nanowire channel like a gate-electrode.

SUMMARY OF THE INVENTION

The inventors have recognized that for practical application of detection devices a high dynamic range is required, often in combination with a low detection limit. It is a problem of the known detector devices that a high sensitivity sensor comes with a low dynamic range.

It is an object of the present invention to provide a nanowire-based sensor which is capable of providing an improved dynamic range, preferably in combination with a high sensitivity.

The object is achieved with the invention as defined by the independent claims. The dependent claims provide advantageous embodiments.

According to the invention there is provided a device for detecting a concentration of a substance in a fluid sample.

A fluid may refer to both a gas and a liquid, and the device is thus suitable for detection of substances in both liquids and gases. Substances can be dissolved or suspended in the sample. Substances can comprise ions, molecules, molecular complexes, particles. In particular they can be substances that can be present in the fluid in low or high concentrations not known beforehand. Substances may be toxic to life requiring adequate concentration determination and also continuous determination preventing extensive preprocessing (dilution) before detection.

That the nanowires are electrically addressable means that it is possible to form an electrical contact to each end of each nanowire in order to perform electrical characterization of the respective nanowires with respect to the nanowire characteristics sensitive for the presence of the substance when the fluid with the substance is brought in the vicinity of the nanowire. The nanowires of the plurality of nanowires are individually addressable. To this end, preferably the nanowires are electrically connected in parallel between multiple electrical contact points. Thus, while one end of each nanowire can be electrically connected to one and the same connection point, each other end then must be individually contacted. Sequential addressing of the nanowire can be achieved using individual gate structures if the nanowires if they are part of one or more transistors. Alternatively, each nanowire is completely individually electrically addressable such that their ends form separate contact points for each nanowire, whether in transistor or not.

When a substance particle or molecule to be detected comes in the vicinity of, or even attaches to the nanowire, the measurable electrical characteristic of the nanowire is influenced according to quantity of the substance and by measurement of the characteristic the quantity of the substance can thereby be deduced. The quantity may be absolute quantity or concentration quantities as in amount of substance per sample volume, sample mass or moles of sample.

The plurality of nanowires comprises at least two nanowires. The amount of nanowires may be equal to and/or larger than 3, 4 5, 10, 20 and even 50. They can be conveniently fabricated in the same patterning process of the device. Each nanowire may be duplicated in order to allow for reliability measurement. The insulating material can be any electrically insulating material. The material prevents in a first instance the short-circuit of the nanowires with the sample fluid. The insulating material preferably is an oxide such as e.g. silicon oxide ($SiO_2$) or Titanium oxide ($TiO_2$) or mixtures thereof. The insulating material can comprise a surface that is exposed to the sample fluid.

The sample compartment is arranged such that the sample is brought in the vicinity of, or in contact with each nanowire including at least the insulating material. Each of the nanowires covered by the respective insulating material is thus arranged for detecting the presence of the substance in the fluid sample through measurement of an electrical characteristic of the nanowire. Any characteristic that is influenced by possible presence of a substance in the sample compartment can be used for the detection purpose. The measured electrical characteristic preferably is for example be the current vs. voltage characteristics of the nanowire. Preferably that characteristic is of a nanowire that is part of a transistor with a gate. By analyzing measured characteristics, the quantity (concentration) of a substance in the sample can be determined. Calibration curves can be used if needed. Preferably there are reference nanowires that are in the vicinity of only the fluid sample, without the substance.

The different nanowires of a plurality of nanowires of a device are configured such that the detection range of each individual nanowire is different. The detection range is the range between the smallest and the largest detectable amount or concentration of a substance in the fluid sample. The smallest amount is defined by the amount of substance that does not give a change in the electrical characteristic of the nanowire, while the largest detectable amount is the amount above which no increase of the same electrical characteristic is further observed, it is related to the saturation signal. The total detection range of the detection device is then given by the ensemble of nanowires, i.e, it is then the sum of the detection range of each individual nanowire.

Accordingly, the present invention is based on the realization that a nanowire based detector with a high dynamic range can be achieved by arranging a number of individually addressable nanowires having different dynamic ranges in parallel for measuring a substance in a fluid. Thereby, the device can be configured so that the total dynamic range of the device is larger than the respective dynamic range of the individual nanowires. Preferably the nanowires of the plurality of nanowires are configured such that the different detection ranges of each one of the plurality of nanowires together form a substantially continuous detection range that is larger than each different detection range. As an example, if a first nanowire can measure a concentration of a substance between 1 and 10, and a second nanowire can measure a concentration between 10 and 100, the dynamic range of each of the nanowires is 10, while the dynamic range of a device comprising the two nanowires in combination would be 100. The device of the invention is advantageous as now samples do not require dilution before providing them to a sensor in order to prevent saturation. Furthermore, a detection device can be made wherein the detection range can be chosen through the number of nanowires and their dynamic range configuration. Moreover, sensitivity of the device (related to detection limit) can be independently set by configuration of the most sensitive nanowire. The device can be designed to be capable of detecting substances with concentration from 100 ppm or larger dosn to 10 ppb. Thus a detection device with improved dynamic range, and state of art sensitivity can be obtained.

The device can accordingly be made using conventional semiconductor materials and is therefore suitable for integration with CMOS-based circuits or with pre-existing lab-on-a-chip solutions using well developed fabrication techniques and requiring minimum adaptation of existing fabrication processes. The device may also advantageously be combined with other types of sensors such as temperature sensors, conductivity sensors etc. Additionally, by selecting different insulating materials for different nanowires, different substances can be detected simultaneously by one device. A further advantage of the present invention is that the compatibility with established processing methods means that sensor devices can be fabricated at a relatively low cost.

The degree of influence that the substance will have on the characteristic of the nanowire depends on compositional as well as structural parameters of the nanowire and additional layers. Each nanowire of said plurality of nanowires can comprises a surface area and a nanowire volume, wherein the ratio of the surface area and the volume is different for the different nanowires of said plurality of nanowires. The larger the ratio, the more sensitive the nanowire is to the presence of substance in its neighborhood and vice versa. The change of detection range, i.e., not necessarily an increase or decrease of the detection range, but simply a different range, comes with a change of the ratio. The nanowire may have a detection surface exposed at its side where the sample compartment extends. The detection surface can be arranged for the detecting of the presence of the substance.

To vary the ratio among the different nanowires of the plurality of nanowires, the length, width or height (thickness) of the nanowire can be used. Preferably then the length or the width are varied while the thickness (perpendicular to substrate layer extension) is kept constant. If the plurality of nanowires is arranged in a planar substrate, then the plurality of different dimensions of the nanowires may be defined in one and the same patterning (masks) step again saving further cost. Also, in many regular substrates, the layer wherein the nanowires are made is a uniform thickness deposited layer of semiconductor such as silicon. Hence standard substrates can be used and etch steps to vary thickness of that layer are not needed thus reducing processing complexity and saving cost. It is preferred that the nanowire width is varied while also the length is kept constant for the plurality of nanowires. The width of nanowires preferably is in the range 8 nm to 1 micrometer. The lower range is in practice limited to smallest feature sizes that can be patterned using lithography or imprint techniques. A preferred range is 50 nm to 500 nm. A more preferred range is 10 nm to 500 nm. Within these ranges there can be nanowires with widths of 10, 15, 20, 25, 30, 50, 100, 200 300, and 400 nm or any combination. This gives nanowires that due to their length still give resistances that can be used in regular IC structures. (Note that the cross section of the nanowire determines its resistance). Lengths of nanowires may be in between 1 to 10 micrometer. They can be lower than 2 micrometer, lower than 1 micrometer, or lower than 500 nm.

Alternatively or additionally, to the dimensional variation between the nanowires of the plurality of nanowires, the thickness of the insulating material and the choice of insulator material covering the nanowire can be changed to implement variations of detection range. Influence of the substance to the characteristics of the nanowire can be through capacitive coupling. Thus, an increase of insulator thickness gives a smaller coupling and less sensitivity and vice versa. Also, variation of material to larger dielectric constant will give increase coupling and increased sensitivity and vice versa. Again adjustment of these parameters comes with different detection range. As the dielectric constant is largely determined by the insulating material which is generally compatible with the substrate materials and processing, the thickness of the layer is the preferred parameter to vary across the nanowires of the plurality of nanowires. The thickness is preferably between 1 nm and 10 nm to give a good sensitivity. If increased sensitivity is needed, the thickness is in the range 1 to 4 nm, most preferably 3 nm. If increased reliability with regard to electrical insulation of the insulating material layer is needed, the thickness preferably is in the range of 6 to 10 nm, most preferably 7 nm. A thickness of 5 nm gives a good compromise between sensitivity and reliability.

As an example, a nanowire with a smaller cross sectional area and a thinner insulating layer will be influenced more by a substance molecule than a wire with a larger area and a thicker insulating layer. Such influence can be via capacitive or inductive changes of the nanowire between situation with substance or without substance.

The device of the invention may be a pH detection device. The insulting layer over the nanowire can be Silicon oxide for this purpose. The surface of silicon oxide generally has Si—OH groups of which the $H^+$ (substance) is reversibly exchangeable with the sample fluid (preferably comprising or consisting of water for good definition of pH). Hence the charge of a surface layer of the silicon oxide (Si—$O^-$) on depends on the pH of the fluid, i.e., high pH reduced bound $H^+$ and large $O^-$ surface charge and low pH, all groups converted to Si—OH and no charge on the surface. The charge determines the conductivity of the nanowire and that can be used as a characteristic of the nanowire to measure.

The device may further comprise a functionalization layer arranged on the nanowire or on the insulating material of at least one of the nanowires. Adding specific functionalization layers on one or more of the nanowires makes it possible to tailor the device to detect a particular substance or group of substances. Plain chemical (covalent) reaction of the substance with the functionalizaiton layer can be used. Alternatively molecular recognition through all sorts or non-covalent reactions, adherence effects can be used.

Furthermore, by adding different functionalization layers to different nanowires, it also becomes possible to detect several different substances or groups of substances simultaneously. Such a device can be used for fingerprinting.

For example, a layer of $TiO_2$ may be arranged as the insulating layer or preferably on the insulating layer of the nanowire to act as a functionalization layer. As $TiO_2$ is known to react with and decompose $CO_2$, a $CO_2$ sensor may be formed. Other functionalization layers can be used. NiOx layer can reduce/oxidise in presence of formaldehyde and can be used to construct a nanowire responsive to formaldehyde. Those skilled in the art will know what layers need be used to recognize specific substances or specific groups of substances. One example may provide layers for detection of blood markers such as those for detection of cardiac disease. In another example the layer is configured to detect carbohydrates or other organic molecules as contamination in e.g. water fluid.

According to one embodiment of the invention, at least two of the nanowires may have different doping concentrations. Varying the doping of the nanowire is an additional means of influencing the electrical characteristics of the nanowire in order to tailor the properties of the sensor for various applications. For example, different doping can be used to realize different threshold voltages of the nanowires. This may provide different sensitivity to the nanowires.

The sample compartment may be configured to allow a fluid to flow over the plurality of nanowires. Thereby, a concentration of a flowing fluid can be detected which for example facilitates the integration of the device in existing lab-on-a-chip devices. Furthermore, the sample compartments may be arranged as an opening in a protective layer so that the contacting structures for electrically contacting the nanowires are protected, thereby preventing a short circuit between the contacting structures in case of a conductive sample fluid.

The part of the substrate (such as e.g., the backside of the substrate) may be used as a gate terminal of a transistor of which at least one of the nanowires of the plurality of nanowires is part. The device then forms a three-terminal device with the backside as gate terminal and the contacting structures as source and drain terminals. Using the backside as a gate terminal can be utilized to enhance the current response for an applied voltage, or it can be used as a switch to control if any current at all may flow through the nanowire. Thereby, the electrical characteristics of the nanowire can be controlled by the gate terminal. The substrate can be patterned to provide individual gate structures to each nanowire if needed.

The device may comprise a second sample compartment allowing for simultaneous detection of more than one substance. A second sample compartment may be used to provide different fluids in contact with arrays of nanowires in order to perform multiple analysis simultaneously. Additionally, the use of two or more sample compartments may further facilitate having nanowires with different characteristics in different sample compartments. In particular, different wire configurations which due to fabrication process complexity may be difficult to combine in one sample compartment can more easily be achieved by using multiple sample compartments.

The device can comprise electrical circuitry connected to each of said nanowires of the plurality of nanowires for readout of the nanowires. The device can be a measurement device ready to use for sample analysis.

The electrical circuitry is preferably configured to:
determine an electrical characteristic of each nanowire of said plurality of nanowires;
determine, for each nanowire of said plurality of nanowires, whether the electrical characteristic indicates that the nanowire is saturated;
identify a subset of nanowires of said plurality of nanowires for which the nanowires are not saturated;
from the subset of nanowires, identify the nanowire having the highest sensitivity; and
based on the determined electrical characteristic of the nanowire having the highest sensitivity, determine the amount of said substance in said fluid.

The device may comprise one or more reference nanowires (each defined according to the invention) that are covered by a reference sample compartment instead of the sample compartment. Such can be easily integrated. Such nanowires can be used to determine the effect of the sample without the substance and to account for such background signal during detection of the sample.

According to the invention there is also provided a method for determining a concentration of a substance in a sample fluid using a device comprising a plurality of individually addressable nanowires.

Measuring the amount or concentration of a substance in a fluid using a high-dynamic range nanowire-based device as described above can be achieved by detecting which of the nanowires are non-saturated and selecting the readout from the most sensitive of the non-saturated nanowires. The resulting amount and/or concentration may of course also be derived from a combination of measured non-saturated nanowires, either by averaging the results from the non-saturated wires or through more complex determination algorithms. Furthermore, it can be assumed that the device is calibrated or that it is otherwise known how the different nanowires respond to different concentrations of a particular substance, thereby making it possible to determine whether a particular nanowire is saturated or not.

According to one embodiment of the invention, the determined electrical characteristic of the nanowires may advantageously be the current as a function of an applied voltage.

In one embodiment of the invention, the device may advantageously be reset by applying a gate voltage so that molecules adhering to the nanowires are removed. It is highly advantageous to be able to reset the device in order to avoid the need to know the measuring history of the device, and also in order to reuse a device that has been saturated. Accordingly, the device may be reset by applying a voltage to the backside of the substrate acting as a gate terminal. The applied gate voltage is of opposite polarity of the operating gate voltage so that electrostatic repulsion causes the molecules adhering to the nanowires to be released, thereby cleaning and resetting the device.

According to one embodiment of the invention, the device may advantageously be reset by heating the device so that molecules adhering to said nanowires are removed. By applying a sufficiently high voltage over the nanowires, so that the temperature in the nanowires is increased through resistive heating, the molecules adhering to the nanowire are released through thermal desorption and the device is thereby reset.

Further effects and features of this second aspect of the present invention are largely analogous to those described above in connection with the first aspect of the invention.

It is noted that the invention relates to all possible combinations of features recited in the claims.

BRIEF DESCRIPTION OF THE DRAWINGS

These and other aspects of the present invention will now be described in more detail with reference to the appended drawings showing an example embodiment of the invention, wherein:

FIG. 3 schematically outlines a method for manufacturing a device according to an embodiment of the invention; and FIG. 4 is a flowchart outlining the general steps of the manufacturing method illustrated in FIG. 3.

DETAILED DESCRIPTION

In the present detailed description, various embodiments of a device according to the present invention are mainly discussed with reference to a device comprising silicon nanowires based on an SOI (silicon-on-insulator) substrate. It should be noted that this by no means limits the scope of the present invention which is equally applicable to devices comprising nanowires based on other semiconductor materials which also may be formed on other types of substrates.

Figure 1:
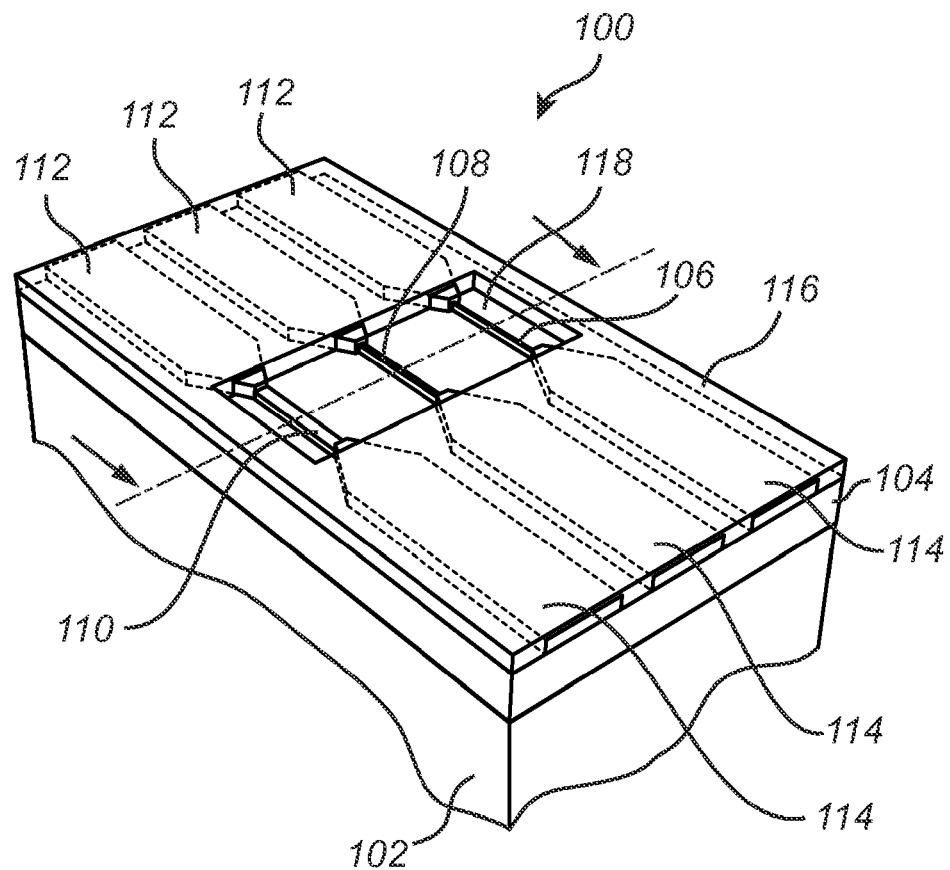
FIG. 1 schematically illustrates a device according to an embodiment of the invention.

FIG. 1 schematically illustrates a device 100 according to an embodiment of the invention. It should be noted that the device in FIG. is not drawn to scale and that the purpose of the drawing merely is to illustrate the general concepts of the invention.

The device 100 comprises a substrate 102, an insulating layer 104 arranged on the substrate 102, three nanowires 106, 108, 110 arranged in parallel are formed in the top silicon layer of an SOI-substrate. There is further illustrated conductive contacting structures 112, 114 which lead to contact pads (not shown) for electrically contacting the respective end of each of the nanowires. The contacting structures 112, 114 may be seen as the source and drain in a three terminal device where the backside of the substrate 102 is used as a gate terminal. In this case, all the contacts are individually contactable giving individually addressable nanowires. However, either contact 112 or 114 can be connected together without losing the individual addressing possibility. A protective layer (electrically insulating layer) 116 is arranged to cover the contacting structures 112, 114 to prevent electrical short-circuit in case of a conductive fluid. An opening 118 in the covering layer forms a sample compartment 118 where a sample fluid may come in contact with the nanowires 106, 108, 110.

Figure 2:
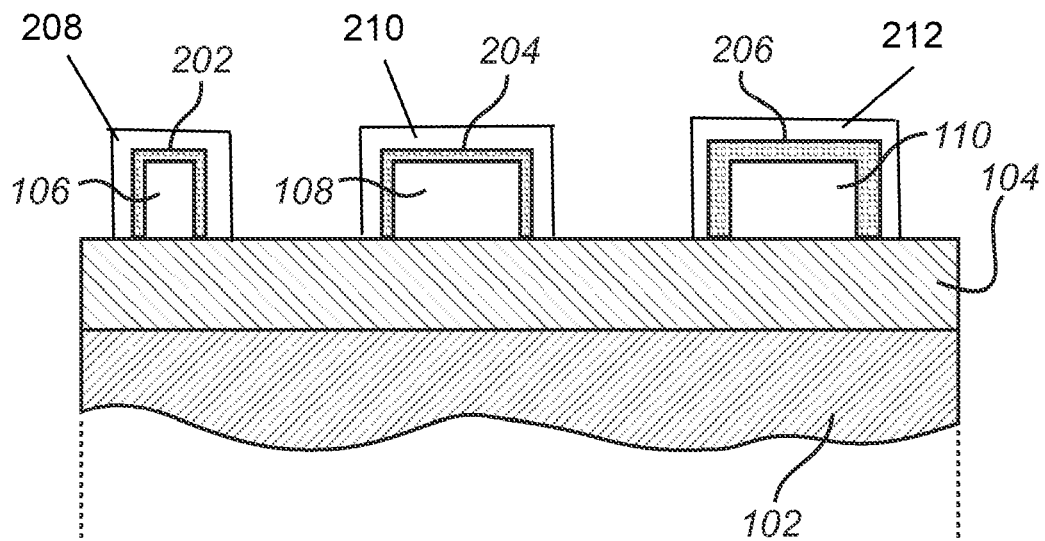
FIG. 2 schematically illustrates nanowires according to various embodiments of the invention.

FIG. 2 schematically illustrates a cross sectional view of the nanowires 106, 108, 110. Each nanowire has a thickness (vertical in the plane of drawing) and a width (horizontal in the plane of drawing). The dimensions of the nanowires typically range from a few nanometers up to hundreds of nanometers. The nanowires are in turn covered by an insulating material 202, 204 206. The insulating material may typically be an oxide such as $SiO_2$ (thermally grown), $TiO_2$ or $Al_2O_3$. Various rare earth-oxides such as $ZrO_2$, $HfO_2$ or the like may also be used. Here it is illustrated that wires within the same device 100 may have different geometries as shown by the different widths of nanowires 106 and 108, and that nanowires having the same geometry may have different thickness of the insulating layer as illustrated by the nanowires 108 and 110 and the corresponding insulating layers 204 and 206. Thereby, nanowires having different electrical characteristics can be formed. A device may typically comprise a large number of nanowires in each sample compartment, such as for example 2 to-50 nanowires or more. Preferably there are 20 to 50 nanowires.

Different functionalization layers 208, 210, 212 can be arranged on the nanowires or the insulating layer of the different nanowires. The functionalization layers may for example be chemical layers such as APTES or metal based layers and oxides such as $TiO_2$, $ZrO_2$ or $HfO_2$. Thereby, by applying different functionalization layers to separate nanowires, an array of sensors can be made that is sensitive to different substances so that a sort of a fingerprint of the sample fluid under analysis can be determined. The different functionalization layers can have different dielectric constants to provide different capacitive coupling to the wires to implement the range differences. Dielectric constants of different materials are widely tabulated in standard texts such as the Handbook of Chemistry and Physics and will not be mentioned here.

The nanowires may be part of a manifold of different types of electrical devices in the device. Such electrical devices include gated devices such as: Field effect based devices having a gate (MOSFET, EGFET) or without a gate (CHEMFET, ISFET, ImmunoFET, HEMFET, ESFET or ENFET.

The device can be a part of or can be a electrical device for gas or fluid purity monitoring. Such may be an air pollution monitoring device. The substance to be detected may be formaldehyde as that is very toxic to humans. Alternatively the device can be a water quality monitoring system. Such devices may have particle filters, or activated carbon filters to remove disturbing side substances from the fluid sample before determining the substance amount.

FIG. 3 schematically outlines the general steps for manufacturing a device according to various embodiments of the invention. FIG. 3 will be discussed with reference to the flowchart of FIG. 4 outlining the general processing steps.

In a first step 402, a SOI substrate is provided comprising a silicon carrier layer 102, a buried oxide (BOX) layer 104 and a top silicon layer 302.

Next step 404, a mask is formed and silicon nanowires and corresponding contact structures 304 are etched in the top silicon layer 302. A nanowire mask may for example be formed through photolithography, e-beam lithography or imprinting. Etching is followed by step 406 comprising deposition of an insulator layer 306. The deposition of an insulator layer may for example be preferable if underetching occurs such that the parts of the BOX layer 104 adjacent to or under the nanowires is damaged during etching of the nanowires. Thereby, any damages resulting from underetching can be repaired by the deposition of the insulator layer 306.

In steps 408 and 410, a protective silicon nitride (SiN) layer 308 is deposited followed by the deposition and patterning of a resist mask 310 exposing the nanowires. Next, the SiN 308 and the insulator layer 306 is removed at the location of the openings in the mask 310 in the regions where the nanowires are located so as to expose the nanowires.

In step 414, the resist mask 310 is removed and in the final step 416, a thermal oxide 310 is grown on the nanowires to form an insulating layer on the nanowire. The thickness and properties of the grown thermal oxide can be controlled by controlling process parameters such as time, temperature and pressure.

The steps 410 to 416 may be repeated for the same device in a way so that different nanowires or subsets of nanowires are exposed by different resist masks, which in turn make s it possible to form nanowires having grown oxide layers 312 of different thicknesses or different properties. The growth of a thermal oxide also makes it possible to control the geometry of the nanowire in by controlling the growth time. As an alternative to thermal oxidation, an oxide may be deposited in step 416, thereby increasing the flexibility in choice of insulating material. Deposition may for example be performed by CVD, ALD, sputtering or other known deposition methods. Thereby, by protecting different wires by different masks, nanowires having different insulating materials and different thickness of the insulating layer can be formed. Furthermore, various functionalizations of the nanowires may also be performed in step 416 by depositing functionalization layers such that a device capable of detecting a wide range of substances can be formed.

Nanowires with different length and/or width can be advantageously made in one set of steps as these are determined by mask dimensions and do not require repeated exposure of different sets of nanowires for depositions etc. In an example embodiment, nanowires having different widths may be formed in step 404. Thereby, after performing the remaining steps as described above, nanowires of different width but with the same insulator material and insulator thickness are provided.

Electrical contacts to the contacting structures are also formed and an ohmic contact is formed on the backside of the substrate to form a backside gate contact. Furthermore, as a result of the CMOS-compatible manufacturing process, a reference transistor is readily realizable on the same chip as a complement to the measurement device to enable differential measurements so that for example temperature changes and other environmental variations can be accounted for.

Furthermore, using the nanowire-based device according to various embodiments of the invention, a method for determining a concentration of a substance in a fluid using the device is provided. In the following, an example embodiment will be discussed with reference to current vs. voltage measurements performed by a measurement arrangement comprising the device. First, the current vs. voltage characteristic for each of the nanowires in a device is determined for a constant gate voltage. Next, it is determined which of the nanowires, if any, are saturated. Current saturation in a nanowire may for example occur if the conducting channel is saturated, i.e. if the conductive channel is completely closed or completely open. Saturation may also occur as a result of surface saturation, i.e. if the entire surface of the nanowire is covered by a substance. Current saturation can for example be determined by comparing the resulting measured characteristic with previously established reference values.

From the subset of non-saturated nanowires, the nanowire having the highest sensitivity is selected. The nanowire having the highest sensitivity is the nanowire able to detect the smallest change in concentration of the particular substance. The sensitivity of each of the nanowires is assumed to be known from manufacturing and/or from earlier calibrations of devices having the same layout.

By identifying the most sensitive, non-saturated nanowire, a result indicating the concentration of a substance can be provided with the highest possible sensitivity for the given device.

If a device capable of detecting different substances is used, the method described above is performed for each subset of nanowires adapted to detect a respective substance.

An example application for the device is as a reversible $CO_2$ sensor. A $CO_2$ sensor can be formed by coating the nanowires with a thin (approximately 1 nm) layer of $TiO_2$. As $CO_2$ has zero dipole moment, it will not induce an electrical field in the channel if attaching to the an insulating layer comprising for example $SiO_2$. Therefore, $TiO_2$ can be used which is known to decompose $CO_2$ into $CO$ and $O_2$, which is polar and thereby induces a field in the conducting channel of the device.

However, oxides such as $TiO_2$, $ZrO_2$ and $HfO_2$ tend to be hydrophilic, thus adsorbing water molecules on the surface which will affect adsorption of $CO_2$, and subsequently affect the electrical measurement. Therefore, in order to increase selectivity and to reduce the interference from adsorbed water, a hydrophobic layer which is permeable to $CO_2$ but not to water molecules may be deposited on the insulating layer. The hydrophobic layer may for example be a polymer such as parylene.

As an alternative to the current vs. voltage analysis, the transient behavior of the device can be analyzed by applying a constant voltage to the source, drain and gate terminals and observing the time dependency of the measured current. Thereby, the concentration of one or more substances in a fluid under analysis can be determined.

Furthermore, a fluidic reference gate for biasing the sample fluid may also be incorporated if it is required for a particular application.

The person skilled in the art realizes that the present invention by no means is limited to the preferred embodiments described above. On the contrary, many modifications and variations are possible within the scope of the appended claims. For example, variations in the manufacturing method and in the choice of materials are fully possible while still adhering to the general concept of the invention.

The invention claimed is:

1. A device for quantitative detection of a substance in a fluid sample, said device comprising:
   a substrate;
   an electrically insulating layer arranged on said substrate;
   a plurality of individually addressable nanowires arranged on said electrically insulating layer, each nanowire of said plurality of nanowires being covered by an individual insulating material, the plurality of nanowires being configured to detect a presence of the substance in the fluid sample through measurement of an electrical characteristic of a nanowire of the plurality of nanowires, each of said nanowire having a length, a width and a thickness;

a sample compartment for comprising said fluid sample,
   wherein said sample compartment is configured to cover at least a part of each nanowire of said plurality of nanowires,
   wherein each of the individual insulating material of the each nanowire is separated from each other, and
   wherein the individual insulating material of each of at least two nanowires of said plurality of nanowires has a thickness that is different with respect to each other to form different detection ranges for the substance.

2. The device as according to claim 1, wherein a combination of the different detection ranges form a substantially continuous detection range that is larger than each different detection range.

3. The device according to claim 1, wherein each nanowire of said plurality of nanowires comprises a surface area and a nanowire volume, wherein a ratio of the surface area and the volume is different for the different nanowires of said plurality of nanowires.

4. The device according to claim 3, wherein the thickness of the nanowires of the plurality of nanowires is substantially the same and one or more of the width and the length of each of the nanowires of said plurality of nanowires is different.

5. The device according to 1, wherein the individual insulating material is the same for each of the nanowires of the plurality of nanowires and wherein the individual insulating material comprises a thickness that is different for each nanowire of the plurality of nanowires.

6. The device according to claim 1, wherein at least one nanowire of said plurality of nanowires comprises at least one functionalization layer configured to interact with the substance.

7. The device according to claim 6, wherein the at least one functionalization layer comprises $TiO_2$.

8. The device according to claim 6, wherein the at least one functionalization layer consists of $TiO_2$.

9. The device according to claim 1, wherein the each one of the at least two nanowires of said plurality of nanowires comprises a functionalization layer configured to interact with the substance, wherein at least two functionalization layers are different from each other.

10. The device according to any claim 1, wherein said sample compartment is configured to include a fluid over said plurality of nanowires.

11. The device according to claim 1, wherein the each one of the at least two nanowires has a different sensitivity.

12. The device according to claim 1, wherein the each one of the at least two nanowires of said plurality of nanowires has a different doping concentration of a dopant.

13. The device according to claim 1, wherein at least one nanowire of the plurality of nanowires forms a channel of a transistor and a part of the substrate is used as a gate terminal of said transistor.

14. The device of claim 1, comprising electrical circuitry connected to each nanowire of the plurality of said nanowires for readout of the nanowires.

* * * * *